United States Patent [19]

Bellet

[11] 4,370,727
[45] Jan. 25, 1983

[54] POCKET CALCULATOR FOR FAMILY PLANNING INCLUDING A THERMOMETRIC PROBE

[75] Inventor: Jean-Marie Bellet, Geneva, Switzerland

[73] Assignee: Bioself International Inc., Nassau, The Bahamas

[21] Appl. No.: 156,446

[22] Filed: Jun. 4, 1980

[30] Foreign Application Priority Data

Jun. 7, 1979 [CH] Switzerland ............... 5336/79

[51] Int. Cl.³ .................. G06F 3/05; G06F 15/42
[52] U.S. Cl. ........................... 364/705; 364/709
[58] Field of Search ............. 364/705, 709, 557, 900

[56] References Cited

U.S. PATENT DOCUMENTS

| | | | |
|---|---|---|---|
| 3,940,742 | 2/1976 | Hudspeth et al. | 364/900 |
| 3,978,325 | 8/1976 | Goldstein et al. | 364/557 X |
| 3,999,050 | 12/1976 | Pitroda | 364/705 |
| 4,151,596 | 4/1979 | Howells | 364/709 |

*Primary Examiner*—David H. Malzahn
*Attorney, Agent, or Firm*—Trexler, Bushnell & Wolters, Ltd.

[57] ABSTRACT

The present invention is intended to solve the problem of the reliable acquisition of accurate temperature data for a miniature calculator provided for the application of family planning methods. The calculator is provided with a receptacle removably carrying a thermometric probe for providing the temperature measurement in a digital form. The circuits of the probe comprise an oscillator including a temperature responsive resistance element to be placed in contact with the area of the temperature to be measured, Tx. The output frequency fx of this oscillator is a function of Tx, and is measured by a counter controlled by a signal formed from a reference frequency fr provided by a reference oscillator and further provided to a frequency divider. A comparator compares the contents of the counter to that of a memory, and in case the counter contents is higher than the stored contents, the comparator controls the entry thereof to the memory so that the probe operates as a maximum thermometer. The contents of the memory is read in serial fashion by the system of the calculator when the probe is replaced into its receptacle.

16 Claims, 10 Drawing Figures

FIG. 1
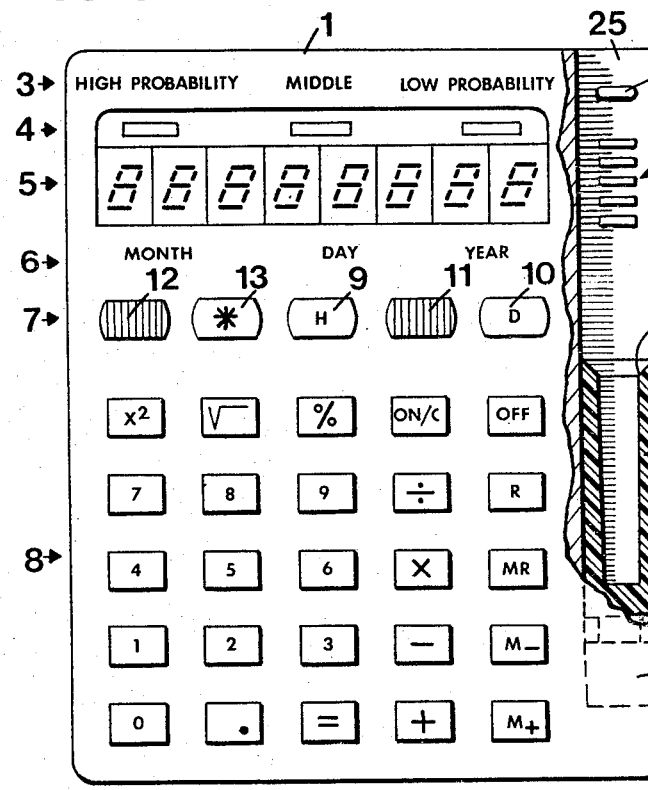
FIG. 2
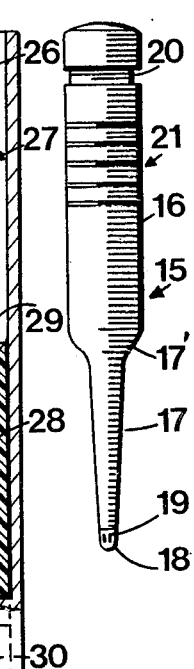
FIG. 3

POCKET CALCULATOR FOR FAMILY PLANNING INCLUDING A THERMOMETRIC PROBE

BACKGROUND OF THE INVENTION

The invention relates to a calculator for family planning, including a thermometric probe.

It is possible to produce at present miniature calculators capable of performing relatively complex calculations for various applications.

Also, calculation methods for family planning are known, for example, the Ogino method. Development of a calculation program for the application of such a method and the incorporation of such a program in a pocket calculator, for example, utilizing a ROM (Read Only Memory) is possible in principle.

However, such a calculator must also be provided with a writable memory such as a Random Access Memory (RAM) for externally supplied data for the application of the method to a particular use. Such externally supplied data includes data related to the date of the catamenial periods of the subject, as well as a curve of body temperature of the subject taken on a day by day basis. These data must be provided during several cycles to allow the proper application of the method to reliably foresee the dates of the next cycle.

The storage of these data in a memory requires a non-volatile memory, i.e., one which maintains its contents even during shut-off of the power supply. The co-pending International Application No. PCT/CH79/00108, filed Aug. 7, 1979, deals with this requirement.

Another problem or requirement concerns the temperature data acquisition. A possible solution consists of taking the temperature by means of a conventional mercury medical thermometer, and to utilize the keyboard of the calculator to input that result into the memory. However, this solution has the disadvantage that it involves a substantial risk of human error both in correctly reading the thermometer and in correctly entering the data with the keyboard. The present invention is directed to simplifying the temperature data acquisition so as to eliminate this risk of human error.

OBJECTS AND SUMMARY OF THE INVENTION

Accordingly, it is a general object of the invention to provide a new and improved pocket calculator for applying a family planning method.

A more specific object is to provide such a calculator wherein the temperature data acquisition is simple and reliable, avoiding the necessity of a manual reading and transcription of the temperature, and thereby avoiding the risk of human error.

In accordance with the present invention, apparatus for family planning comprises a pocket calculator and an independent, cooperating thermometric probe, said pocket calculator comprising a casing, a control keyboard, a display, electronic calculating and control means, memory means arranged for application of a family planning method, and a receptacle for removably receiving said thermometric probe which comprises a probe body ended by a thermometric sensor, a measuring circuit connected to the sensor and providing temperature information in the form of digital data corresponding to the temperature of the sensor, and output contact means for outputting said temperature information. The receptacle of the calculator includes mating contact means selectively connectable with the output contact means of the probe. The receptacle contact means being coupled with the calculating and control means, the calculating and control means being arranged to read and store said digital data temperature information, there being no connection between the calculator and the probe when the probe is removed from the receptacle for measuring a temperature.

BRIEF DESCRIPTION OF THE DRAWINGS

The invention will be better understood from the following description of the illustrated embodiment together with reference to the drawing, in which:

FIG. 1 is a front plan view, partially broken away and partially in section of a pocket calculator for family planning;

FIG. 2 is an elevational view of a thermometric probe for use with the calculator of FIG. 1;

FIG. 3 is a top view of the calculator of FIG. 1;

FIG. 6b is a back view of a portion of the calculator of FIG. 6a;

DETAILED DESCRIPTION OF THE ILLUSTRATED EMBODIMENT

Figure 4:
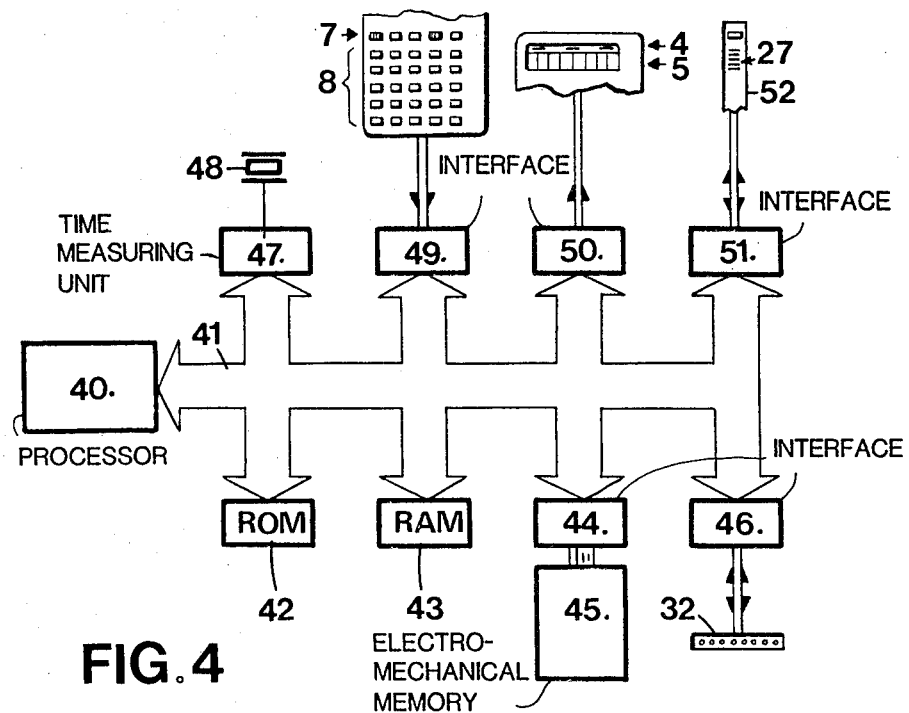
FIG. 4 is a diagrammatic representation of a microprocessor system for the calculator of FIG. 1.

A calculator is represented in FIG. 1, comprising a casing 1 on which is provided suitable display elements 4, 5, surrounded with inscriptions 3, 6 and control keys 7, 8.

A plurality of digital display elements and a plurality of digit keys 8 are similar to the corresponding part of a conventional, four function calculator. The upper display elements 4 comprise three areas each arranged facing one inscription of the inscription line 3. These display elements 4 are intended to indicate the result of a forecasting calculation applying a method of family planning. In particular, display elements 4 indicate the probability for intercourse at a given date to be followed by a pregnancy, e.g., if the probability is high, middle or low.

The digital display elements 5 display numerical data and arithmetical results as an ordinary calculator numerical display, in response to the manipulation of the keyboard 8. Moreover, this digital display 5 also allows a display of a date, the left-most two digits giving the month, the next digit not being activated, the two next digits giving the day, the following digit not being activated, and the last or right-most two digits indicating the year. This arrangement also permits a display of the time, a blinking or the moving of the seconds serving to differentiate the display of the time from the display of a date.

Among the keys 7, a key 9 "H" controls the display of the time and other keys 10–13 are specifically for use of the calculator in applying a family planning method.

The key 10 "D" controls the display of the date and also allows the keyboard entry of another date, for which a forecasting calculation is requested. The keys 11 and 12 allow the entry into memory of the date of the menstrual periods.

If the date to be entered is the current date, it may be shown on the display 5 by depression of the key D. If it is another date, that other date may be entered by means of the digital keyboard, by depressing the key D after the keyboard entry of the numeral of the month, the numeral of the day and the numeral of the year, respectively. The entered date is displayed. Then the keys 11 and 12 are simultaneously depressed, and the entered date is then registered or stored in memory as the date of the beginning of the period. This operation modifies the stored data, accordingly, the entry thereof requires the described sequence of actuation of keys to reduce the risk of an unintended modification. The date is displayed according to the Anglo-Saxon disposition, that is to say, month, day, year, in correspondence with the inscriptions 6. But it is obvious that other dispositions may be provided, in particular the inscriptions 3 and 5 being translated into another language or form, such as the European designation of dates as day, month, year.

The key 13 "*" controls the calculation of a forecast for the displayed date on the digital display 5, the result showing on the upper display 4; a double depression of the same key "*" controls the calculation of a forecast giving the interval about an ovulation during which the probabilities of a pregnancy are maximum. Both extreme dates are displayed alternately with a period of one to two seconds.

The calculator case 1 also provides a receptacle 25 for the thermometric probe 15 of FIG. 2. This receptacle 25 mounts a spring-loaded holding tab 26 provided to engage an annular retaining groove 20 provided on the periphery of the body 16 of the probe 15. The receptacle 25 also mounts a plurality of contacts 27 provided to engage a like plurality of annular contacts 21 arranged on the body 16 of the probe 15. The bottom of the receptacle 25 is filled in by an axially moveable sleeve 28 having a frustro-conical opening 29 and intended to receive the thin part 17 of the probe 15, at the end of which is a temperature sensor 18. It may be noted that the length of the cavity of the sleeve is longer than the length of the thin part 17 of the probe, so as to prevent the temperature sensor 18 from touching the bottom of the cavity, the probe being held by a shoulder portion 17' thereof at the frustro-conical opening 29.

It may also be noted that the body 16 is cylindrical and both broader and longer than the thin part 17, so that when the probe 15 is introduced into its receptacle 25, the thin part 17 faces the frustro-conical opening 29 without abutting on to the edges of this opening. The axially moveable sleeve 28 cooperates with a pawl and spring mechanism 30 so arranged than when the sensor 15 is in place and depressed about 2 mm further into the receptacle 25, the mechanism 30 reacts and pushes the sleeve back and hence the probe 15 so that the probe 15 may be readily grasped and removed from the receptacle 25 to be used. When the probe 15 is at rest in the receptacle 25, it is just flush with the surface of the casing 1. On the temperature sensor portion 18 of the probe 15, a moisture sensor 19 has also been provided to detect contact with a mucosa.

The upper face of the calculator case 1, as best viewed in FIG. 3, shows the end of the probe 15, and also shows an outer connector with a plurality of contacts 32 arranged in a cavity 33. The cavity is sealed by a cover (not shown) including a retaining tongue cooperating with a retaining groove 34.

The calculator has a configuration of a microprocessor system represented in FIG. 4, of which certain parts are conventional. The system comprises a processor 40 connected by a bus 41 to memories and to peripherals. Among the memories are: a ROM memory 42 for the programs and the fixed data, a RAM memory 43, a special memory 45 comprising bi-stable electromechanical relays and its interface 44. There is an example of this latter memory 45 in the International Application No. PCT/CH79/00108 previously mentioned. In this regard, the relays used are miniature relays having high stability for preserving the stored data information even if the power supply is cut off.

The system represented in FIG. 4 further includes a time measuring unit 47, operating with a quartz crystal 48. The system accommodates as peripherals the keyboard comprising the keys 7, 8, and the display devices 4, 5, for example, of the LCD type (liquid crystals), with their respective interfaces 50, 51. The system also accommodates the probe 15 including the contacts 27 by means of an interface 51 and the outer connector contacts 32 by means of an interface 46.

Figure 5:
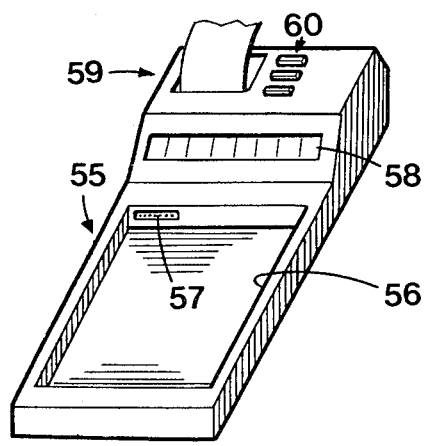
FIG. 5 is a perspective view of a monitoring apparatus for use with the calculator of FIG. 1.

The apparatus 55 of FIG. 5 is intended to perform certain control operations on the calculator. In principle, such an apparatus is intended for use by a gynecologist or other qualified personnel of a family planning center. The apparatus 55 performs a "start-up" operation upon the calculator which makes possible the proper application of a method by the untrained user. Also, the apparatus 55 provides access to the stored contents of the calculator in order to draw for example the curve of the body temperatures measured day by day, which provides a useful indication for a consultation to the gynecologist. One of the "start-up" operations concerns the initial time and date setting after providing the calculator with batteries. In principle, this operation is done only once for the service life of the batteries; hence, this time reset is not possible during normal use, since the user might inadvertently or incorrectly modify the data, whereby the resulting forecast could be inaccurate.

The apparatus 55 comprises the receptacle 56 intended to receive a calculator of the type previously described with reference to FIGS. 1 and 3. Within the receptacle 56, a connector 57 is provided to cooperate with the outer connector 32 of the calculator. The apparatus 55 includes a display 58, control keys 60 and a printer 59 allowing for example the establishment of a temperature curve, day by day, from the data stored in the calculator. The apparatus also performs the initial time and date settings of the calculator.

The system of FIG. 4 utilizes a ROM containing a fixed program, including the initial time and date content for the time measuring unit, and updating thereof by orders given through the digital keyboard 8, but only providing that the calculator is connected to a control apparatus 55, and that an appropriate key has been activated on said control apparatus, this key acting on the microprocessor system of FIG. 4 via the outer connector 32 and its interface 46.

Figure 6A:
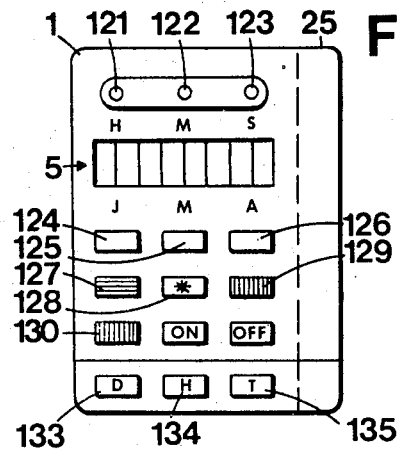
FIG. 6a is a front elevation of another embodiment of the calculator.

FIG. 6a illustrates another embodiment of the calculator, which differs from the embodiment of FIG. 1 in that it has a simpler keyboard and in that it is not intended to be connected to a control apparatus, such as the apparatus 55 of FIG. 5.

On a case 1, there is provided a special display consisting of three electro-optical elements 121, 122, 123, respectively red, yellow and green, intended to indicate the result of a forecast calculation according to the following convention: high probability: red; mean: yellow; low: green. The digital display 5 allows a display of the time, a date or a temperature. The key "H" 134 allows to control the display of the present time and the key "D" 133 controls the display of the actual date. The key "*" 128 controls a forecast calculation for that date, or by double action, the calculation of the interval about the ovulation where the probability of a pregnancy is maximum. The keys J, M and A, 124, 125 and 126, allow changing of the displayed date. Upon action on one of the keys, the corresponding numeral increases, the day for the key J, the month for the key M and the year for the key A. The key 127 allows reverse action of keys 124–126 which then, decrease the respective numerals. The keys 129, 130 allow the entry of the displayed date as the date of the first day of the menstrual period.

Figure 6B:
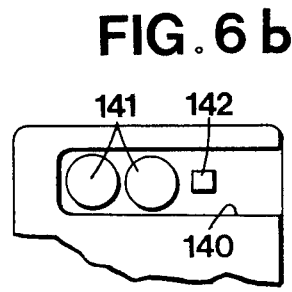

FIG. 6b shows partially the back of the calculator of FIG. 6a with a housing 140 for the batteries 141, this housing 140 also containing a special control key 142. This key 142 is normally inaccessible, as it is concealed by the cover of the housing of the batteries. This key is intended to allow certain control or adjusting operations effected by a person specially trained in a family planning center, or by the gynecologist. Actuation of this key 142 activates a program provided for the initial time and date settings of the calculator, upon the starting of operation thereof, as well as providing access to the memory to read the stored contents.

Briefly, the calculator is held in one hand, and the housing of the battery 140 uncovered to give access to the key 142. The other hand remains free to act upon the keyboard. While keeping the control key 142 depressed, the key "T" 135 is actuated, and the display 9 shows then the earliest stored temperature, alternately with its date, and when the key "T" is again depressed, the display shows the temperature of the following day, alternately with its date, and so on, which allow to establish the temperature curve. Further, for the day of the periods, the letter "r" is displayed together with the temperature, and for dates of an interval about the ovulation, the light element 121 is on. For the entry of the date and the time, the keys 124–127 are actuated to make the present date appear and it is entered by simultaneous actuation of the key "D" 133 and of the entry key 129, the control key 142 being maintained depressed. To input the time, the key "H" 134 is actuated, and if required the displayed time is modified by means of the keys 124–127, and it is input by simultaneous actuation of the "H" key 134 and the entry key 129, the control key 142 being maintained depressed.

Figure 7:
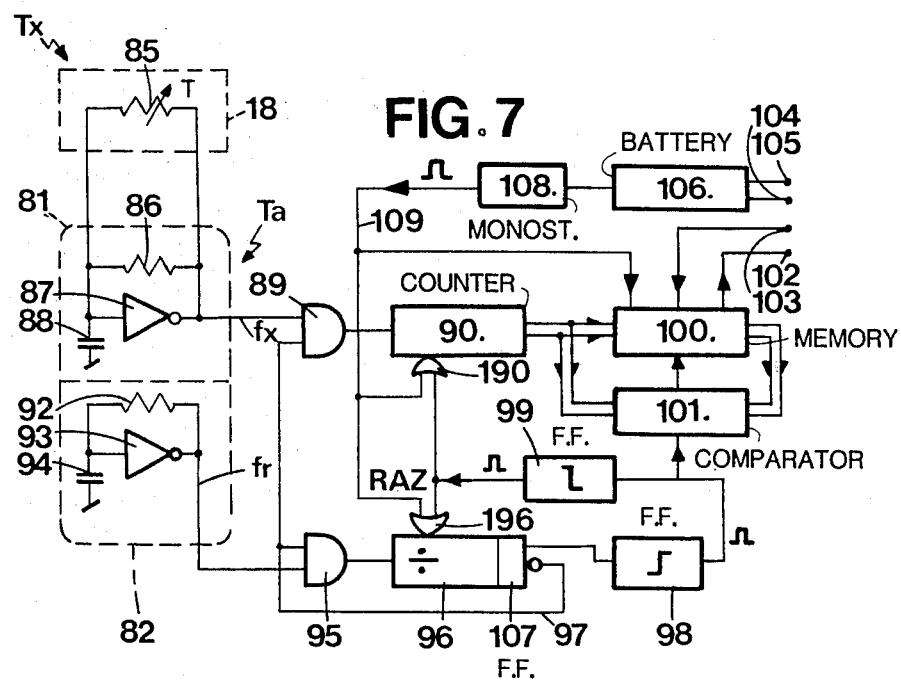
FIG. 7 is a circuit schematic of the circuits of the thermometric probe of FIG. 2.

FIG. 7 shows an exemplary electrical diagram for a thermometric probe intended for use with the pocket calculator for family planning. In this circuit, the sensor 18 is, during measuring, brought to the temperature to be measured Tx. The sensor is comprised of a temperature responsive resistance element or NTC 85, for example of 600 Kohms, with a characteristic of 5%/°, in other words 30 Kohms/° about its rated value. This NTC 85 is connected to the circuit of a relaxation oscillator 81 formed by an inverter trigger 87 and of a network RC comprising a capacitor 88 and a resistor 86 in parallel with the NTC 85. The resistor 86 is optional, particularly where the resistance 85 has a good linear characteristic in the working range. The oscillator 81 provides logical pulses with a frequency fx depending on the temperature Tx. These pulses pass via an AND gate 89 into a counter 90.

The circuit of FIG. 7 also comprises a reference oscillator 82 of similar construction to the first oscillator. This oscillator 82 comprises an inverter trigger 93 and a network RC with a capacitor 94 and a resistor 92. The reference oscillator 82 has a frequency fr of the same order of magnitude as fx, for example fr being the geometrical average between the maximum and the minimum of the working range of fx. This frequency fr is provided, via an AND gate 95 to a divider 96 which divides it by a number representing the inverse of the relative precision required for the measurement. For example, it may be supposed that fx is in a range varying about 100,000 Hz, fr being equal 100,000 Hz, and that a precision of 1 millionth for the counting of the frequency fr is desired, the divider stage 96 being then a divider of frequency per a factor of 1 million, or close to 1 million, for example $2^{20}$; ($2^{10}=1024$). The divider 96 is ended by a flip-flop 107 of which the inverted output 97 controls the AND gates 89 and 95, and of which the non-inverted output controls two successive monostable flip-flops 98 and 99, the first one serving for entry of the result of frequency counting, and the second serving for a reset. The output of the second flip-flop 99 is provided to OR gates 190 and 196 which control the reset inputs of the counter 90 and of the divider 96, respectively. The counter 90 is connected to a memory 100 and to a first input of a comparator 101, the second input of this comparator being connected to the memory 100. To transfer the contents of the memory to the system, the memory 100 includes a serial output line 102 and a synchronization input line 103 for proper synchronization of the serial data transfer therefrom. The circuit further includes control supply and units 106, 108 connected to the terminals 104, 105, and 109. The terminals 102 to 105 inclusive lead to the annular contacts 21 of the probe.

In addition to its electrical power supply function, the supply unit 106 has the function of initial resetting of the counter 90, of the divider 96 and of the memory 100. For this purpose, the unit 106 controls a monostable flip-flop control unit 108 of which the output 109 is connected to a reset input of the memory 100, and to OR gates 190 and 196 controlling the reset input of the counter 90 and of the divider 96, respectively.

The operation of this circuit is as follows.

When the probe 15 is placed in the receptacle 25, the terminals 104 and 105 change the power supply or battery 106 from the calculator, the circuit being arranged so as to deactivate the other elements of the circuit of FIG. 7 as long as the probe 15 is in the receptacle 25. When the probe is removed with a view to taking the temperature, its circuits are activated, the counter 90, the divider 96 and the memory 100 being reset. As soon as the probe is removed, both oscillating circuits supply respectively their frequencies fx and fr. When the divider 96 has effected one cycle, its final stage 107 is set to logic 1 and the line 97 inhibits the AND gates 89 and 95, which blocks the counting. At the same time, the monostable sends a control pulse to actuate the comparator 101. If the contents of the counter 90 is higher than the contents of the memory 100, the contents of the counter 90 is input in the memory 100. At the end of the pulse of the monostable 98, the monostable 99 sends a reset pulse to the counter 90 and to the divider 96, including its terminal stage 97, which again activates the AND gates 89 and 95, so that a new measuring cycle is started.

If the measurement of the new cycle is a higher result, in other words, if the temperature Tx has increased, then the action of the comparator is to effect the inputting of the latter value. Hence, the probe operates as a maximum thermometer. The advantage of this arrangement is the following: when the person removes the probe after having taken the temperature and, subsequently, the sensor temperature returns to ambient temperature, the rectal temperature, which is higher, remains stored. When the probe is replaced in the calculator, the microprocessor system may read the stored result via the terminals 102 and 103. The terminal 102 transmits synchronization pulses and the terminal 103 transmits a sequence of binary values representing the contents of the memory 100.

It should be noted that the reference oscillator 82 is physically located adjacent to the measuring oscillator 81, and it is similar, except for the NTC element 85. Further, both oscillators 81, 82 are at substantially the same temperature Ta. Therefore, if the frequency fx of the first oscillator, a function of the temperature Tx, is further influenced by a thermal drift or a power supply drift acting on the circuit 81, one can expect to have the reference frequency fr effected in the same direction and by the same drift acting on the reference oscillator 82. Hence, if such a drift slows down for example fx, it will slow down fr in the same proportion, which will increase the time duration of the counting, so that at the end the drift effect will be cancelled.

The logic part of the circuit of FIG. 7 is built from relatively simple elements such as counters, gates, registers. However, for the functions of the circuit of FIG. 7, or for adding more complex functions, it may be desirable to use a microprocessor. Accordingly, in the circuit of FIG. 8, a similar measuring oscillator 81 is connected to a sensor 18, and a similar reference oscillator 82 is provided, both of which oscillators 81, 82 are connected to a control circuit 80 which may be a microprocessor. The circuit 80 is connected to a suitable connector leading to the annular contacts 21 of the probe 15.

Figure 8:
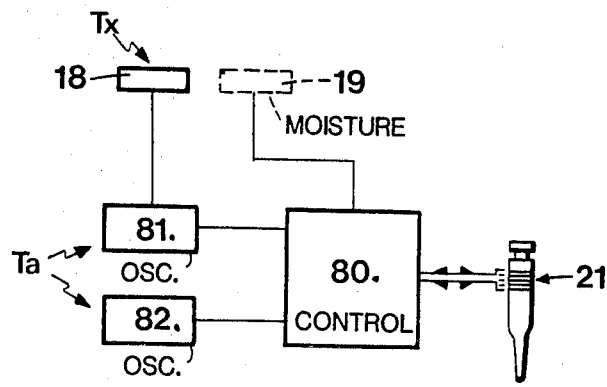
FIG. 8 is a block diagram of an alternate for of the circuits of the thermometric probe of FIG. 2.

Also, the circuit of FIG. 8 may include a moisture detector 19. The temperature to be measured is in principle the rectal temperature, and the purpose of the moisture detector is to provide an indication of the contact with the rectum wall, sufficiently moist to make the appropriate detector react. The signal provides an additional indication with regard to the validity of the measurement. According to the conventional method, the temperature must be taken on waking. Therefore, the time may also be used as a condition for a valid measurement. This condition is of course controlled by the system of the calculator, which consults its time measuring unit at the moment when the probe is replaced after having been taken out. The system may also be arranged for example so as to consider as non-valid a measurement of the temperature effected on the same day as a previous measurement, or at a time which is too remote with respect to the usual waking time, or a temperature which is outside the range of physiological temperatures. The program may be readily modified as well to recognize the difference between the change of temperature connected to the catamenial cycle, and a temperature change of pathological origin, such as a light fever or hypothermy. It is evident that such a disease may otherwise make the method inaccurate. These criteria are applied by the program of the calculator.

Figure 9:
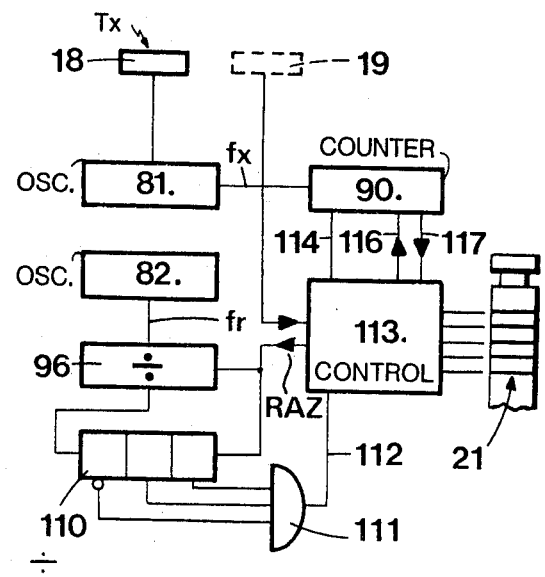
FIG. 9 is a block diagram of another embodiment of the circuits of the thermometric probe of FIG. 2.

Another condition affecting validity of the temperature measurement is that the probe 15 be in thermal balance with the area to be measured. To this end, delay means may be provided on the probe 15 itself. FIG. 9 represents a circuit of a probe 15 provided with such a delay means. The circuit comprises the sensor 18 connected to the measuring oscillator 81 of which the output is connected to the counter 90, and the reference oscillator 82 of which the output is connected to the frequency divider 96. The divider 96 is followed by a further divider 110 with three binary stages. The inverted output of the first of these stages and the normal output of the two other stages are connected to respective inputs of a three-input AND gate 111 of which the output 112 is provided to a control circuit 113. This circuit 113 controls the counter 90 via the line 114. The counter 90 is further arranged to provide a reading in a serial mode by means of a read-out line 117 and a synchronization line 116.

The operation is as follows. Initially, the counter 90 and the dividers 96 and 110 are set on zero. The period at the output of the divider 96 is supposed, as an example, to be equal to 10 seconds. The output 112 of the gate 11 is in the state "1" when the counter 110 is in the state "6" or "110" in binary, this state having a duration of 10 seconds and taking place between the 60th and 70th second after the start of the operation.

The circuit 113 is arranged to actuate the counter 90, via the line 114, exactly during the time when the line 112 is on "1", whereafter it sets off the oscillators 81, 82. When the probe 15 is put back in its receptacle 25, the circuit 113 ensures the transfer of the number counted by the counter 90 to the system of the calculator. In this circuit the reference oscillator 82 is used not only as a time basis for the counting duration, which allows to measure fx with respect to fr, but also as a time basis for a delay.

While preferred embodiments have been illustrated and described herein, the invention is not limited thereto. On the contrary, various alternatives, changes or modifications may become apparent to those skilled in the art from the foregoing. Such alternatives, changes, and modifications are to be considered as forming a part of the invention, insofar as they fall within the spirit and scope of the appended claims.

The invention is claimed as follows:

1. In a pocket calculator for family planning including a casing, a control keyboard, a display, electronic calculating and control means and a memory arranged for application of a family planning method, the improvement comprising: a receptacle in said casing for receiving a removable thermometric probe, said thermometric probe comprising a probe body ended by a thermometric sensor, a measuring and storing circuit connected to the sensor for providing and storing temperature information in the form of digital data corresponding to the temperature of the sensor, and output contact means for outputting said temperature information, the receptacle of the calculator including mating contact means, the receptacle contact means being coupled with the calculating and control means, the calculating and control means being arranged to read and store in the memory said digital data temperature information, there being no connection between the calculator and the probe when the probe is removed from the receptacle.

2. The combination according to claim 1, the calculator memory further including means for storing initial time and date data and further including a time measuring circuit means operatively coupled with said memory for, during storage of said temperature information, simultaneously measuring and storing in said memory time and date data associated with said temperature data information.

3. The combination according to claim 2 and further including control input means in addition to the keyboard, normally inactive and activatable to permit modification of the initial time and date in the memory means.

4. The combination according to claim 1 or claim 3, and further including additional control means, normally inactive, and allowing access to the memory at least to read the stored data.

5. The combination according to claim 4, and further including outer connector means for connection to a monitoring device.

6. The combination according to claim 5, wherein the calculating and control means are operatively coupled to said outer connector means to provide to the monitoring device, via said outer connector means, said stored data.

7. The combination for use with a pocket calculator for family planning, said calculator including a casing, a keyboard, a display, electronic calculating and control means and memories arranged for application of a family planning method, said thermometric probe comprising: an elongate probe body including a thermometric sensor at one end thereof, a measuring circuit means carried in said probe body and coupled with said thermometric sensor and responsive thereto for providing digital data temperature information corresponding to the sensor temperature, and contact means for selective connection with mating contact means of the calculator for transfer of said digital data temperature information thereto, said thermometric probe being substantially self-contained and requiring no connection with said calculator for measuring and providing said digital data temperature information.

8. The combination according to claim 7, wherein the sensor comprises a variable impedance element of which the value depends on the temperature, and the measuring circuit means comprises a first oscillating circuit coupled with said variable impedance element of which the frequency depends upon the value of that impedance, a second oscillating circuit providing a reference frequency, and count means for counting the first frequency and controlled by a signal depending on the reference frequency and providing said digital data information corresponding to said temperature.

9. The combination according to claim 8, characterized in that the second oscillating circuit is located closely to and similar to the first oscillating circuit, except for the sensor, so that if the frequency of the first oscillator is further influenced by a power supply drift or a thermal drift, the frequency of the second oscillator is then influenced in the same direction by the same drift, so that the effect of said drift is substantially cancelled.

10. The combination according to claim 7 or claim 9 and further including delay means coupled with said measuring circuit means for delaying the measuring for a predetermined time after the probe is taken out of contact with the calculator in order to allow the user to place the probe and in order to allow the sensor to achieve thermal balance with the area to be measured.

11. The combination according to claim 7 and further including a moisture detecting device close to the thermometric sensor for providing a signal indicating that the probe is in contact with a mucosa, the measuring circuit means being responsive to said signal for providing said temperature data information only in the presence of said signal provided by said moisture detecting device.

12. The combination according to claim 7, and further including a memory and a comparator, and wherein said measuring circuit means initially provides said digital data temperature information to the memory and thereafter provides periodically said digital data temperature information to said comparator, and said comparator compares this data with the content of the memory and, if this data information exceeds the content, said measuring circuit means inputs the data into the memory, so that the probe operates as a maximum thermometer.

13. The combination according to claim 7, and further including a rechargeable self-contained power supply for powering said probe to perform a measurement, said power supply being coupled with said contact means for recharging from the calculator via the contact means and mating contact means.

14. Apparatus for family planning comprising a pocket calculator and an independent, cooperating thermometric probe, said pocket calculator comprising a casing, a control keyboard, a display, electronic calculating and control means, memory means arranged for application of a family planning method, and a receptacle for removably receiving said thermometric probe which comprises a probe body ended by a thermometric sensor, a measuring circuit means connected to the sensor and providing temperature information in the form of digital data corresponding to the temperature of the sensor, and output contact means for outputting said temperature information, the receptacle of the calculator including mating contact means selectively connectable with the output contact means of the probe, the calculating and control means being coupled with the receptacle contact means to read and store said digital data temperature information, there being no connection between the calculator and the probe when the probe is removed from the receptacle for measuring a temperature.

15. Apparatus according to claim 7 or claim 14, said thermometric probe further comprising electronic control logic means coupled with the measuring circuit means for controlling the measuring circuit means and for receiving said digital data temperature information, memory means for storing said digital data temperature information and self-contained power supply means.

16. Apparatus according to claim 1, said thermometric probe further comprising electronic control logic means coupled with the measuring and storing circuit for controlling the measuring and storing circuit and for receiving said digital data temperature information, memory means for storing said digital data temperature information and self-contained power supply means.

* * * * *